United States Patent
Xavier et al.

(10) Patent No.: US 12,208,151 B2
(45) Date of Patent: *Jan. 28, 2025

(54) HAIR TREATMENT COMPOSITION

(71) Applicant: L'OREAL, Paris (FR)

(72) Inventors: Liliana Xavier, Mountainside, NJ (US); Kazumitsu Kawakami, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/050,096

(22) Filed: Oct. 27, 2022

(65) Prior Publication Data

US 2023/0132734 A1    May 4, 2023

Related U.S. Application Data

(60) Provisional application No. 63/273,194, filed on Oct. 29, 2021.

(30) Foreign Application Priority Data

Jan. 12, 2022 (FR) ........................ 2200201

(51) Int. Cl.

| | | |
|---|---|---|
| *A61K 8/34* | (2006.01) | |
| *A61K 8/06* | (2006.01) | |
| *A61K 8/20* | (2006.01) | |
| *A61K 8/73* | (2006.01) | |
| *A61K 8/81* | (2006.01) | |
| *A61Q 5/00* | (2006.01) | |

(52) U.S. Cl.
CPC .............. *A61K 8/342* (2013.01); *A61K 8/062* (2013.01); *A61K 8/20* (2013.01); *A61K 8/731* (2013.01); *A61K 8/737* (2013.01); *A61K 8/8158* (2013.01); *A61K 8/817* (2013.01); *A61Q 5/002* (2013.01)

(58) Field of Classification Search
CPC .......... A61K 8/342; A61K 8/062; A61K 8/20; A61K 8/731; A61K 8/8158; A61Q 5/002
USPC ...................................................... 424/70.1
See application file for complete search history.

(56) References Cited

U.S. PATENT DOCUMENTS

| | | |
|---|---|---|
| 9,610,241 B2 | 4/2017 | Cabourg et al. |
| 2003/0134761 A1 | 7/2003 | Sebillotte-Arnaud et al. |
| 2004/0120914 A1 | 6/2004 | Decoster et al. |
| 2004/0131576 A1 | 7/2004 | Decoster et al. |
| 2005/0058616 A1 | 3/2005 | Dupuis |
| 2008/0299154 A1 | 12/2008 | Barrios et al. |
| 2009/0071493 A1 | 3/2009 | Nguyen et al. |
| 2010/0015189 A1 | 1/2010 | Perron et al. |
| 2010/0129307 A1 | 5/2010 | Singer et al. |
| 2011/0256084 A1 | 10/2011 | Dixon et al. |
| 2013/0149274 A1 | 6/2013 | Nguyen et al. |
| 2013/0167861 A1 | 7/2013 | Lopez et al. |
| 2013/0167862 A1 | 7/2013 | Lopez et al. |
| 2013/0251656 A1 | 9/2013 | Khenniche et al. |
| 2014/0186283 A1 | 7/2014 | Cabourg et al. |
| 2014/0186284 A1* | 7/2014 | Sha .......................... A61Q 5/12 424/70.13 |
| 2014/0366907 A1 | 12/2014 | Fack et al. |
| 2015/0157540 A1 | 6/2015 | Rizk et al. |
| 2015/0283040 A1 | 10/2015 | DeGeorge et al. |
| 2015/0283041 A1 | 10/2015 | Benn et al. |
| 2015/0283042 A1 | 10/2015 | Benn et al. |
| 2018/0177708 A1 | 6/2018 | Lee et al. |
| 2018/0280270 A1* | 10/2018 | Rughani ................. A61K 8/447 |
| 2019/0008750 A1 | 1/2019 | Sakaguchi et al. |
| 2019/0125650 A1 | 5/2019 | Lee et al. |
| 2020/0170894 A1 | 6/2020 | Park et al. |
| 2020/0405618 A1 | 12/2020 | Kadish et al. |
| 2021/0093541 A1 | 4/2021 | Desai et al. |
| 2021/0267871 A1 | 9/2021 | Parikh |

FOREIGN PATENT DOCUMENTS

FR    3109883 A1    11/2021

OTHER PUBLICATIONS

"The HLB system—a time saving guide to emulsifier selection". Chemmunique (Ed.), (1980). ICI Americas Inc. Delaware, USA ( Year: 1980).*
Preliminary Search Report and Written Opinion issued on Sep. 20, 2022 for corresponding French Application No. FR 2200201.

* cited by examiner

*Primary Examiner* — Isaac Shomer
*Assistant Examiner* — Bryan James Rego
(74) *Attorney, Agent, or Firm* — POLSINELLI PC

(57) ABSTRACT

Hair treatment compositions and methods for using them is described. The hair treatment compositions include: (a) one or more fatty alcohols; (b) one or more cationic surfactants; (c) one or more cationic polymers; (d) one or more nonionic polymers; (e) citric acid, salts thereof, or combinations thereof; and (f) water.

18 Claims, No Drawings

HAIR TREATMENT COMPOSITION

CROSS-REFERENCE TO RELATED APPLICATIONS

This application claims benefit of U.S. Ser. No. 63/273,194 filed Oct. 29, 2021, and benefit of French Application No. FR 2200201, filed on Jan. 12, 2022, which are incorporated herein by reference in their entirety.

FIELD OF THE DISCLOSURE

The present disclosure relates to hair-treatment compositions and methods for treating hair with the hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Hair can become dry or damaged for various reasons, e.g., weather exposure, poor nutrition, mechanical treatments (e.g. brushing hair), styling treatments using chemicals, dying, heat, nutrition, etc. Even cleansing products can remove hair's natural oils causing dryness, which can lead to a dull appearance and to split ends.

Chemical treatments include, for example, hair bleaching and coloring, permanents, waving products, and relaxing treatments (straightening treatments). These chemical treatments change the look of hair by changing its physical structure, which inevitably causes a certain degree of damage to the hair. Environmental factors, such as salt water, sunlight, and heat, are also known to damage hair. Damaged hair is characterized by unnatural changes to the protein structure of the individual hair strands or shafts. Damage results in split ends, dry straw-like hair, hair that is easily broken, and hair that is "frizzy" and unmanageable. Because the visible portion of hair is dead, it has no ability to regenerate itself. There are numerous over the counter and salon treatments that purport to repair damaged hair. These include conditioners, hot oil treatments, hydrolyzed proteins, vitamin formulations, and exotic fruit, leaf, or root extracts. These treatments, however, provide only limited improvement to the hair. Therefore, hair repair technologies that restore the properties of hair back to their natural level are desired.

The popularity and usage of oils for dry hair treatments has increased due to their effectiveness and simplicity. Commonly used oils include olive oil, mineral oil, avocado oil, apricot kernel oil, rice bran oil, and coconut oil. However, these treatments can leave the hair feeling greasy. In addition, the effects are not usually seen after more than several hours (e.g. 8 hours) of treatment and several treatments are usually required, making it time consuming and labor intensive.

There is still a need for providing improved manageability of hair, for example, improved hair alignment, reduced unwanted volume (especially reduced frizz), and increased shine. There is also a need to develop hair care products that can impart other benefits at the same time in addition to caring and conditioning benefits, such as styling, volume, shaping, and curl definition (for curly or wavy hair).

SUMMARY OF THE DISCLOSURE

The instant disclosure relates to hair treatment compositions and methods that provide advantageous effects to hair. For example, the hair treatment compositions improve cosmetic attributes such as softness, shine, conditioning, and healthy appearance. The hair treatment compositions include cationic polymers and nonionic polymers; and include citric acid, a salt thereof, or a combination thereof. The inventors found that the ratio of cationic polymers to nonionic polymers and the citric acid, salt thereof, or combination thereof influences the stability and the desirable cosmetic properties of the compositions.

The hair treatment compositions of typically includes:
(a) one or more fatty alcohols;
(b) one or more cationic surfactants;
(c) one or more cationic polymers;
(d) one or more nonionic polymers;
(e) citric acid, a salt thereof, or a combination thereof; and
(f) water;
wherein all weight percentages are based on the total weight of the composition.

The weight ratio of the one or more cationic polymers (c) to the one or more nonionic polymers (d) is typically from about 2.9:1 to 1:2.9. In addition, the pH of the composition is typically from about 3 to about 6.

Silicones can optionally be included in the hair treatment compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the hair treatment compositions of the instant case can be free or essentially free from dimethicones, amomdimethicones, dimethiconols, cyclosiloxanes, siloxanes, etc.

The hair treatment compositions are aqueous compositions and are typically in form of an oil-in-water emulsion. The fatty alcohols, and optionally additional fatty materials (referred to as "fatty compounds") primarily form the fatty phase of the emulsion. The aqueous phase is formed by water, and optionally may include one or more water-soluble solvents. The compositions typically include high amounts of water, for example, at least 50% by weight, preferably at least 60% by weight, and more preferably, at least 65% by weight.

Fatty alcohols, as is well known in the art, are aliphatic alcohols, for example, primary alcohols having a carbon chain from about 8 to about 30 carbon atoms, preferably from about 12 to about 22 carbon atoms. Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

Cationic surfactants, as is well known in the art, are is a type of surfactant with a positive charge on their hydrophilic end. Non-limiting examples of useful cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chlofride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyldiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

Cationic polymers, as is well known in the art, are polymers bearing a positive charge or incorporating cationic entities in their structure. Non-limiting examples of useful cationic polymers include cationic cellulose derivatives (e.g., polyquaternium-10), quaternized hydroxyethyl cellulose, cationic starch derivatives, cationic guar gum derivatives, cationic proteins and cationic protein hydrolysates, quaternary diammonium polymers, copolymers of acrylamide and dimethyldiallyammonium chloride, polyquaterniums (e.g., polyquaternium-10), and a mixture thereof. In some instances, cationic cellulose derivative and/or polyquaterniums, such as polyquaternium-10 are particularly useful.

Nonionic polymers, as is well known in the art, are polymers lacking a net electrical charge. Non-limiting examples include polysaccharides, polysaccharide derivatives (e.g., guar gum, guar derivatives, cellulose gum, cellulose derivatives, starch, starch derivatives), homopolymers and copolymers of ethylene oxide having a molar mass equal to or greater than 10,000 g/mol, polyvinyl alcohols, homopolymers and copolymers of vinylpyrrolidone, homopolymers and copolymers of vinylcaprolactam, homopolymers and copolymers of polyvinyl methyl ether, and mixtures thereof. Many nonionic polymers have thickening properties and are sometimes referred to as "nonionic thickening polymers." Nonionic thickening polymers can be useful in the compositions of the instant disclosure, for example, when a certain degree of thickening is desired. In some instance, guar gum and/or nonionic guar derivatives are particularly useful, for example, hydroxypropyl guar.

Nonlimiting examples of salts of citric acid include sodium citrate, sodium citrate tribasic, citric acid trisodium salt, trisodium citrate, sodium citrate dihydrate, sodium citrate tribasic dihydrate, citric acid trisodium salt dihydrate, trisodium citrate dihydrate, potassium citrate, tripotassium citrate, potassium citrate tribasic, citric acid tripotassium salt, potassium citrate monohydrate, tripotassium citrate monohydrate, potassium citrate tribasic monohydrate, citric acid tripotassium salt monohydrate, citric acid disodium salt, citric acid disodium salt sesquihydrate, sodium hydrogencitrate, sodium hydrogencitrate sesquihydrate, disodium hydrogen citrate, disodium hydrogen citrate sesquihydrate, sodium citrate dibasic, sodium citrate dibasic sesquihydrate, potassium citrate monobasic, potassium dihydrogen citrate, citric acid monopotassium salt, sodium citrate monobasic, sodium dihydrogen citrate, citric acid monosodium salt, and the like. In a preferred embodiment, the salts of citric acid include sodium citrate (monosodium citrate, disodium citrate, and/or trisodium citrate), potassium citrate (also known as tripotassium citrate), and combinations thereof.

Fatty compounds other than the fatty alcohols discussed above, may optionally be included in the hair treatment compositions of the instant disclosure. The term "fatty compound" is interchangeable with the term "fatty material." As is well known in the art, fatty compounds are compounds that are not soluble (or only sparingly soluble in water; they are hydrophilic and can often be solubilized in organic solvents. They include materials such as oils, fats, waxes, hydrocarbons, fatty esters, fatty acids, etc. Non-limiting examples of useful fatty compounds include oils, waxes, alkanes (paraffins), fatty acids, fatty esters, triglyceride compounds, lanolin, hydrocarbons, derivatives thereof, and mixtures thereof.

The hair treatment compositions of the instant disclosure may optionally include one or more water-soluble solvents. Water-soluble solvents are organic compounds and are also referred to as "water-miscible solvents." Non-limiting examples of water-soluble solvents include glycerin, $C_{1-6}$ mono-alcohols, polyols (polyhydric alcohols), glycols, and a mixture thereof.

The hair treatment compositions may optionally include one or more nonionic surfactants. Nonionic surfactants, as is well known in the art, are surfactant molecules that generally do not undergo ionization when dissolved in water. Non-limiting examples of nonionic surfactants include alkyl polyglucosides; alcohols, alpha-diols, alkylphenols and esters of fatty acids, being ethoxylated, propoxylated or glycerolated; ethoxylated fatty esters; glyceryl esters of fatty acids; fatty alcohol ethoxylates; alkyl phenol ethoxylates; fatty acid alkoxylates; and mixtures thereof. In some instances, nonionic surfactants such as polyoxyethylenated C8-C30 fatty acid esters of sorbitan can be particularly useful.

The hair treatment compositions of the instant disclosure are particularly useful as a rinse-off product, i.e., a product that is applied to the hair and temporarily allowed to remain on the hair, for example, massaged into the hair, and subsequently rinsed from the hair prior to styling the hair. Thus, the instant disclosure relates to methods for treating the hair with the hair treatment compositions. The methods include applying a hair treatment composition to the hair and subsequently rinsing the hair treatment composition from the hair. The hair treatment compositions may be used as a conditioner composition that is applied to the hair before or after shampooing the hair; or it can be used as a conditioner composition that used without shampooing the hair.

Typically, the hair treatment composition is applied to wet or damp hair, massaged into/throughout the hair, and subsequently rinsed from the hair before optionally drying and/or styling the hair. The hair treatment composition may be allowed to remain on the hair prior to rinsing for a period of time, for example, a period of time of about 10 seconds to about 10 minutes, prior to rinsing from the hair. The hair treatment composition may be allowed to remain on the hair prior to rinsing for a period of time of at least 5 minutes, for example, at least 5 minutes to about 15 minutes.

In certain embodiments, the hair treatment compositions of the instant disclosure may be used as a leave-on product, i.e., a product that is applied to the hair prior to and/or while styling the hair and remains on the hair after the hair is styled. The leave-on product can be applied to wet, damp, or dry hair after shampooing and optionally conditioning the hair. The leave-on product may also be applied to wet, damp, or dry hair independent of shampooing and/or conditioning.

In certain embodiments, the hair treatment compositions of the instant disclosure are particularly useful in conjunction with chemical hair treatments. For example, the hair treatment compositions can be applied to chemically treated hair as a rinse-off or leave-on product. Also, the hair treatment compositions can be used as a pre-treatment or post-treatment before of after chemically treating hair, i.e., before or after treating the hair with chemically reactive products such as oxidative hair coloring/lightening compositions and hair relaxer and/or straightening compositions.

The methods of treating hair, according to the procedures discussed above, are useful for conditioning the hair. The procedures are also useful in methods for improving natural look and feel of the hair, reducing hair frizz, improving hair smoothness, hair alignment, and/or hair shine. The methods also relates to increasing the hydrophobicity of the hair.

The hair treatment compositions disclosed herein may be provided in a kit. For example, one or more of the hair treatment compositions of the instant disclosure may be included in a kit that also include one or more additional hair treatment compositions, for example, one or more cleansing compositions, in particular, one or more shampoo compositions. Each of the one or more hair treatment compositions in the kit are separately contained. In some instances, the kits include one or more hair treatment compositions according to the instant disclosure and one or more shampoo compositions, wherein each of the one or more hair treatment compositions and the one or more shampoo compositions are separately contained.

DETAILED DESCRIPTION OF THE DISCLOSURE

The instant disclosure relates to hair-treatment compositions and to methods for treating hair using the hair-treatment compositions. The hair-treatment compositions are typically in the form of an oil-in-water emulsion and include:

The hair treatment compositions typically include:
(a) one or more fatty alcohols:
(b) one or more cationic surfactants;
(c) one or more cationic polymers;
(d) one or more nonionic polymers;
  wherein the weight ratio of (c) to (d) is from 2.9:1 to 1:2.9;
(e) about 0.1 to about 5 wt. % of citric acid, a salt thereof, or a combination thereof; and
(f) about 55 to about 90 wt. % of water.
  wherein the composition has a pH of about 3 to about 6 and all weight percentages are based on the total weight of the composition.

In various embodiments, the cosmetic composition may optionally include (g) one or more fatty compounds other than the fatty alcohols of (a); and/or (h) one or more water-soluble solvents; (i) and/or one or more nonionic surfactants; and/or (j) one or more miscellaneous ingredients.

The hair treatment compositions are aqueous composition that are preferably oil in water emulsions or dispersions. Silicones can optionally be included in the hair treatment compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the hair treatment compositions of the instant case can be free or essentially free from dimethicones, amomdimethicones, dimethiconols, cyclosiloxanes, siloxanes, etc.

(a) Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair treatment compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C═C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C═C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair treatment compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

The one or more fatty alcohols in the hair treatment composition may be the predominant ingredient, other than water. In other words, the hair treatment composition may include a higher total amount of the one or more fatty alcohols than any other ingredient, or class of ingredients. Accordingly, the hair treatment composition may include a higher total amount of the one or more fatty alcohols (a) than the total amount of the one or more cationic surfactants (b); a higher total amount of the one or more fatty alcohols (a) than the total amount of the one or more cationic polymers (c); a higher total amount of the one or more fatty alcohols (a) than the total amount of the one or more nonionic polymer (d); a higher total amount of the one or more fatty alcohols (a) than the total amount of citric acid, salt thereof, and/or combination thereof (e); a higher total amount of the one or more fatty alcohols (a) than the total amount of the one or more fatty compounds other than fatty alcohols (g); a higher total amount of the one or more fatty alcohols (a) than the total amount of the one or more water-soluble solvents (h); a higher total amount of the one or more fatty alcohols (a) than the total amount of the one or more nonionic surfactants (i).

In some instances, the hair treatment compositions may have a higher total amount of the one or more fatty alcohols (a) than the total combined weight percent of the one or more cationic surfactants (b) and the one or more nonionic surfactants (j). Furthermore, in some instances, the hair treatment composition may have a higher total amount of the one or more fatty alcohols (a) than the total combined weight percent of the one or more cationic surfactants (b), the one or more nonionic surfactants (i), and any additional surfactants that may optionally be present, e.g., amphoteric/zwitterionic surfactants.

In some instances, the weight ratio of the total amount of the one or more fatty alcohols (a) to the one or more cationic surfactants (b) is at least 1.5:1 ((a):(b)). Furthermore, the weight ratio of the total amount of the one or more fatty alcohols (a) to the one or more cationic surfactants (b) may be at least 1.8:1, 1.9:1, 2:1, 2.1:1, or 2.2:1 ((a):(b)). Thus, the ratio of (a):(b) may be from 1.8:1 to about 5:1, about 1.9:1 to about 5:1, about 2:1 to about 5:1, about 2.1:1 to about 5:1, about 2.2:1 to about 5:1, about 2.2:1 to about 5:1, about 1.8:1 to about 4:1, about 1.9:1 to about 4:1, about 2:1 to about 4:1, about 2.1:1 to about 4:1, about 2.2:1 to about 4:1, about 2.2:1 to about 4:1, about 1.8:1 to about 3:1, about 1.9:1 to about 3:1, about 2:1 to about 3:1, about 2.1:1 to about 3:1, about 2.2:1 to about 3:1, about 2.2:1 to about 3:1, including any combination, sub-combination, range, or sub-range thereof by weight, based on the total weight of the hair treatment composition.

The hair treatment compositions typically include about 1 to about 20 wt. % of one or more fatty alcohols, based on the total weight of the hair treatment composition. The hair treatment compositions may include, for example, from about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, about 5 to about 20 wt. %, about 5 to about 15 wt. %, about 5 to about 12 wt. %, about 5 to about 10 wt. %, about 6 to about 20 wt. %, about 6 to about 15 wt. %, about 6 to about 12 wt. %, or about 7 to about 12 wt. % of the one or more fatty alcohols, including any combination, sub-combination, range, or sub-range thereof by weight, based on the total weight of the hair treatment composition.

(b) Cationic Surfactants

The term "cationic surfactant" as defined by the instant disclosure is a surfactant that may be positively charged when it is contained in the hair treatment compositions according to the disclosure. The cationic surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactant comprises cetrimonium chloride, behentrimonium chloride, and mixtures thereof. Behentrimonium Chloride, also described by the technical names that include 1-Docosanaminium, N,N,N-Trimethyl-, Chloride, and N,N,N-Trimethyl-1-Docosan-aminium Chloride, is the quaternary ammonium salt that conforms to the formula:

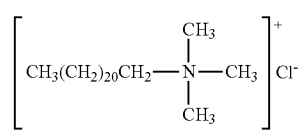

Additional nonlimiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$ hydrocarbon-based chain.

Examples of quaternary ammonium salts that may especially be mentioned include: those corresponding to the general formula below:

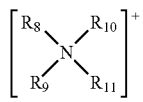

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyal, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Also useful are quaternary ammonium salts of imidazoline, such as, for example, those of formula below:

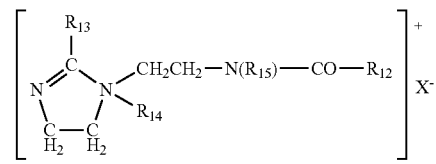

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo.

Useful quaternary diammonium or triammonium salts includes those of the formula:

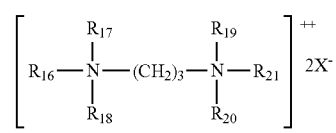

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$) ($R_{17a}$)($R_{18a}$)N—($CH_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75).

Useful cationic/cationizable surfactants, including cationizable surfactants together with an acid neutralizer, include those of the general structure R4-A-R5-B wherein R4 is a saturated or unsaturated, straight or branched alkyl chain with 8 to 24 C atoms, R5 is a straight or branched alkyl chain with 1 to 4 C atoms, A is selected from:

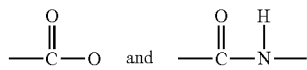

and B is selected from

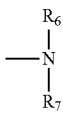

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

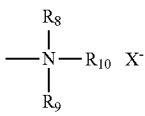

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines and fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

The hair treatment compositions according to the instant disclosure typically include about 1 to about 10 wt. % of one or more cationic surfactants, based on the total weight of the hair treatment composition. The hair treatment compositions may include about 1 to about 8 wt. %, about 1 to about 6 wt. %, about 1 to about 5 wt. %, about 2 to about 10 wt. %, about 2 to about 8 wt. %, about 2 to about 6 wt %, about 2 to about 5 wt. %, about 3 to about 10 wt. %, about 3 to about 8 wt. %, or about 3 to about 6 wt. % of the one or more cationic surfactants, including any combination, sub-combination, range, or sub-range thereof by weight, based on the total weight of the hair treatment composition.

(c) Cationic Polymers

Cationic polymers as defined in the context of the instant disclosure are polymers bearing a positive charge or incorporating cationic entities in their structure. The cationic polymers can comprise mixtures of monomer units derived from amine- and/or quaternary ammonium-substituted monomer and/or compatible spacer monomers. Cationic polymers often provide conditioning benefits to the hair treatment compositions and therefore may be referred to as "cationic conditioning polymers." Non-limiting examples of cationic polymers include copolymers of 1-vinyl-2-pyrrolidine and 1-vinyl-3-methyl-imidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). Additionally or alternatively, the cationic conditioning polymers may include or be chosen from cationic guar gum derivatives, such as guar hydroxypropyltrimonium chloride.

Preferred cationic polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic).

Non-limiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Non-limiting examples of cationic guar include guar hydroxypropyltrimonium chloride, hydroxypropyl guar hydroxypropyltrimonium chloride, Non-limiting examples of cationic starch include starch hHydroxypropyltrimonium chloride, hydroxypropyl oxidized starch PG trimonium chloride, and a mixture thereof.

The hair treatment composition may include or be chosen from polyquaterniums. For example, the hair treatment composition may include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful. A particularly preferred and useful cationic polymer is polyquaternium-10.

The cationic polymers may be a polyquaternium. In certain embodiments, the cationic surfactants may be polyquaterniums selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

In some embodiments, the one or more cationic polymers are chosen from cationic proteins and cationic protein hydrolysates (e.g., hydroxypropyltrimonium hydrolyzed wheat protein), quaternary diammonium polymers (e.g., hexadimethrine chloride), copolymers of acrylamide and dimethyldiallyammonium chloride, and mixtures thereof.

The hair treatment compositions according to the instant disclosure typically include about 0.1 to about 5 wt. % of one or more cationic surfactants, based on the total weight of the hair treatment composition. The hair treatment compositions may include about 0.1 to about 4 wt. %, about 0.1 to about 3 wt. %, about 0.1 to about 2 wt. %, about 0.1 to about 1.5 wt. %, about 0.2 to about 5 wt. %, about 0.2 to about 4 wt. %, about 0.2 to about 3 wt. %, about 0.2 to about 2 wt. %, about 0.2 to about 1.5 wt. % of the one or more cationic polymers, including any combination, sub-combination, range, or sub-range thereof by weight, based on the total weight of the hair treatment composition.

(d) Nonionic Polymers

Nonionic polymers often provide thickening properties to hair treatment compositions and therefore may be referred to as "nonionic thickening polymers." Non-limiting examples of nonionic polymers include polyvinylpyrrolidone, polyacrylamide, a neutral polysaccharide, and derivatives (such as ethers and esters) thereof. Examples of polysaccharide derivatives include neutral gums (such as guar gum and hydroxypropylguar), cellulose ethers (such as hydroxyethylcellulose (HEC), methylhydroxyethylcellulose (MHEC), ethylhydroxyethylcellulose (EHEC), methylethylhydroxyethylcellulose (MEHEC), hydroxypropylcellulose (HPC), hydroxypropylmethylcellulose (HPMC), and hydrophobized derivatives (e.g., HM-EHEC) thereof), and starch and derivatives (e.g., dextrin) thereof.

Among the nonionic thickening agents that may be mentioned are:

(1) Celluloses modified with groups comprising at least one fatty chain; examples that may be mentioned include: hydroxyethylcelluloses modified with groups comprising at least one fatty chain, such as alkyl, arylalkyl or alkylaryl groups, or mixtures thereof, and in which the alkyl groups are preferably C8-C22, for instance the product NATROSOL PLUS GRADE 330 CS ($C_{16}$ alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol, (2) Hydroxypropyl guars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc, (3) Copolymers of vinylpyrrolidone and of fatty-chain hydrophobic monomers; examples that may be mentioned include: the products ANTARON V216 or GANEX V216 (vinylpyrrolidone/hexadecene copolymer) sold by the company I.S.P. the products ANTARON V220 or GANEX V220 (vinylpyrrolidone/ eicosene copolymer) sold by the company I.S.P., (4) Copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name ANTIL 208, (5) Copolymers of hydrophilic methacrylates or acrylates and of hydrophobic monomers comprising at least one fatty chain, for instance the polyethylene glycol methacrylate/lauryl methacrylate copolymer, (6) Polyurethane polyethers comprising in their chain both hydrophilic blocks usually of polyoxyethylenated nature and hydrophobic blocks, which may be aliphatic sequences alone and/or cycloaliphatic and/or aromatic sequences, (7) Polymers with an aminoplast ether backbone containing at least one fatty chain, such as the PURE THIX compounds sold by the company Sud-Chemie.

In some instances, the nonionic polymers are chosen from polysaccharides, nonionic derivatives of polysachaides, associative polymers, and mixtures thereof. In some cases, preferred nonionic polymers include sclerotium gum, guar gums, hydroxyalkyl celluloses optionally modified with a hydrophobic group, such as hydroxyethylcelluloses, hydroxymethylcelluloses optionally modified with a hydrophobic group, and inulins optionally modified with a hydrophobic group.

In a preferred embodiment, the one or more nonionic polymers are chosen from methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, methylhydroxypropyl starch, and a mixture thereof.

Hydroxypropyl guar gum is a particularly preferred nonionic polymers for use in the hair treatment compositions of the instant disclosure.

The hair treatment compositions typically include about 0.1 to about 5 wt. % of the one or more nonionic polymers, based on the total weight of the hair treatment composition. The hair treatment compositions may include about 0.1 to about 4 wt. %, about 0.1 to about 3 wt. %, about 0.1 to about 2 wt. %, about 0.1 to about 1.5 wt. %, about 0.2 to about 5 wt. %, about 0.2 to about 4 wt. %, about 0.2 to about 3 wt. %, about 0.2 to about 2 wt. %, about 0.2 to about 1.5 wt. % of the one or more nonionic polymers, including any combination, sub-combination, range, or sub-range thereof by weight, based on the total weight of the hair treatment composition.

Combined Amount of (c) and (d)

In various embodiments, the combined amount of the one or more cationic polymers (c) and the one or more nonionic polymers (d) may be less than 4 wt. %, less than 3.5 wt. %, less than 3 wt. %, less than 2 wt. %, less than 1 wt. %; or from about 0.1 to about 3.5 wt. %, about 0.1 to about 3 wt. %, about 0.1 to about 2.5 wt. %, about 0.1 to about 2 wt. %, about 0.1 to about 1.5 wt. %, about 0.1 to about 1 wt. %, about 0.2 to about 3.5 wt. %, about 0.2 to about 3 wt. %, about 0.2 to about 2.5 wt. %, about 0.2 to about 2 wt. %, about 0.2 to about 1.5 wt. %, or about 0.2 to about 1 wt. %.

(e) Citric Acid and Salts Thereof

Nonlimiting examples of salts of citric acid include sodium citrate, sodium citrate tribasic, citric acid trisodium salt, trisodium citrate, sodium citrate dihydrate, sodium citrate tribasic dihydrate, citric acid trisodium salt dihydrate, trisodium citrate dihydrate, potassium citrate, tripotassium citrate, potassium citrate tribasic, citric acid tripotassium salt, potassium citrate monohydrate, tripotassium citrate monohydrate, potassium citrate tribasic monohydrate, citric acid tripotassium salt monohydrate, citric acid disodium salt, citric acid disodium salt sesquihydrate, sodium hydrogencitrate, sodium hydrogencitrate sesquihydrate, disodium hydrogen citrate, disodium hydrogen citrate sesquihydrate, sodium citrate dibasic, sodium citrate dibasic sesquihydrate, potassium citrate monobasic, potassium dihydrogen citrate, citric acid monopotassium salt, sodium citrate monobasic, sodium dihydrogen citrate, citric acid monosodium salt, and the like. In a preferred embodiment, the salts of citric acid include sodium citrate (monosodium citrate, disodium citrate, and/or trisodium citrate), potassium citrate (also known as tripotassium citrate), and combinations thereof. In a further preferred embodiment, the salts include sodium citrate (monosodium citrate, disodium citrate, and/or trisodium citrate).

Typically, the cosmetic compositions include a combination of citric acid and salts of citric acid, which will exist in an equilibrium of the acid and its conjugate base. It is particularly preferred that the compositions include a combination of citric acid and sodium citrate (monosodium citrate, disodium citrate, and/or trisodium citrate).

The hair treatment compositions according to the instant disclosure typically include about 0.1 to about 5 wt. % of citric acid, salts thereof, or combinations thereof, based on the total weight of the hair treatment composition. The hair treatment compositions may include about 0.1 to about 4 wt. %, about 0.1 to about 3.5 wt. %, about 0.2 to about 5 wt. %, about 0.2 to about 4 wt. %, about 0.2 to about 3.5 wt. %, about 0.5 to about 5 wt. %, about 0.5 to about 4 wt. %, about 0.5 to about 3.5 wt. %, about 1 to about 5 wt. %, about 1 to about 4 wt. %, or about 1 to about 3.5 wt. % of citric acid, salts thereof, or combinations thereof, including any combination, sub-combination, range, or sub-range thereof by weight, based on the total weight of the hair treatment composition.

(f) Water

The hair treatment compositions in accordance with the instant disclosure typically include about 55 to about 90 wt. % of water, based on the total weight of the hair treatment composition. The hair treatment compositions may include about 60 to about 90 wt. %, about 65 to about 90 wt. %, about 70 to about 90 wt. %, about 55 to about 85 wt. %, about 60 to about 85 wt. %, about 70 to about 85 wt. %, about 55 to about 80 wt. %, about 60 to about 80 wt. %, about 65 to about 80 wt. %, or about 70 to about 80 wt. % of water, including any combination, sub-combination, range, or sub-range thereof by weight, based on the total weight of the hair treatment composition.

(g) Fatty Compounds

The hair treatment compositions may optionally include one or more fatty compounds. The term "fatty compounds" is interchangeable with the "fatty material. Fatty compounds are known as compounds that are not soluble (or only sparingly soluble) in water; they are hydrophilic and are often solubilized in organic solvents. They include materials such as oils, fats, waxes, hydrocarbons, fatty esters, fatty acids, etc. Non-limiting examples of useful fatty compounds include oils, waxes, alkanes (paraffins), fatty acids, fatty esters, triglyceride compounds, lanolin, hydrocarbons, derivatives thereof, and mixtures thereof. Fatty compounds are described by the International Federation Societies of Cosmetic Chemists, for example, in Cosmetic Raw Material Analysis and Quality, *Volume I: Hydrocarbons, Glycerides, Waxes and Other Esters* (Redwood Books, 1994), which is incorporated herein by reference in its entirety.

Non-limiting examples of fatty compounds include oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof.

Fatty Alcohol Derivatives

The fatty compounds may include one or more fatty alcohol derivatives, which are different from fatty alcohols (component (b)). Fatty alcohol derivatives include fatty esters derived from one or more fatty alcohols. Fatty alcohol derivatives also include alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acids

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

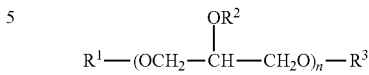

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Waxes

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oils

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

The total amount of fatty compounds in the hair treatment compositions, if present, may vary. For example, the total amount of fatty compounds may be about 0.01 to about 20 wt. %, about 0.01 to about 15 wt. %, about 0.01 to about 10 wt. %, about 0.01 to about 5 wt. %, about 0.01 to about 3 wt. %, about 0.1 to about 20 wt. %, about 0.1 to about 15 wt. %, about 0.1 to about 10 wt. %, about 0.1 to about 5 wt. %, about 0.1 to about 3 wt. %, about 1 to about 20 wt. %, about 1 to about 15 wt. %, about 1 to about 10 wt. %, about 1 to about 5 wt. %, or about 1 to about 3 wt. %, including any combination, sub-combination, range, or sub-range thereof by weight, based on the total weight of the hair treatment composition.

(h) Water-Soluble Solvents

The hair-treatment compositions may optionally include one or more water-soluble solvents. The term "water-soluble solvent" is interchangeable with the term "water-miscible solvent" and relates to organic compounds that are liquid at 25° C. and at atmospheric pressure (760 mmHg), and have a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

Non-limiting examples of water-soluble solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of are ethylene glycol, propylene glycol, butylene glycol, hexylene glycol, propane diol, and glycerin. The organic solvents can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some instances, polhydric alcohols may be particularly useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the hair treatment compositions include one or more water-soluble solvents chosen from chosen glycerin, $C_{1-6}$ mono-alcohols, polyols (polyhydric alcohols), glycols, and a mixture thereof. In an even more preferred embodiment, the hair treatment compositions include one or more water-soluble solvents chosen from glycerin, $C_{1-6}$ mono-alcohols, and a combination therefore, in particular, a combination of glycerin and a monoalcohol chosen from isopropanol, ethanol, and mixtures thereof.

The amount of water-soluble solvents, if present, may vary but typically the hair treatment compositions include about 0.1 to about 20 wt. %, of the one or more water-soluble solvents, based on the total weight of the hair treatment composition. The hair treatment composition may include about 0.1 about 15 wt. %, about 0.1 to about 12 wt. %, about 0.1 to about 10 wt. %, about 0.1 to about 8 wt. %, about 0.5 to about 20 wt. %, about 0.5 to about 15 wt. %, about 0.5 to about 12 wt. %, about 0.5 to about 10 wt. %, about 0.5 to about 8 wt. %, about 1 to about 20 wt. %, about 1 to about 15 wt. %, about 1 to about 12 wt. %, about to about 10 wt. %, about 1 to about 8 wt. %, about 2 to about 20 wt. %, about 2 to about 15 wt. %, about 2 to about 12 wt. %, about 2 to about 10 wt. %, about 2 to about 8 wt. % of the one or more water-soluble solvents, including any combination, sub-combination, range, or sub-range thereof by weight, based on the total weight of the hair treatment composition.

(i) Nonionic Surfactants

The hair treatment compositions may optionally include one or more nonionic surfactants. Nonionic surfactants can be useful for enhancing emulsification. Therefore, nonionic surfactants may also be referred to as nonionic emulsifiers.

The nonionic surfactants include surfactants/emulsifier that are useful for forming a water-in-oil emulsion. For example, the nonionic surfactants may be chosen from alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof. In some instances, polyglycerolated C8-C30 fatty acid esters are particularly useful include those chosen from polyglycerolated esters of C12-C18 fatty acids, in particular lauric, myristic, palmitic, stearic or isostearic acid, having from 2 to 16 mol of glycerol.

Nonlimiting examples of polyglycerolated fatty acid esters include polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof. In some instances, polyglyceryl-2 isostearate is particularly useful.

The nonionic surfactants/emulsifiers may be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms and especially from 16 to 30 carbon atoms.

Mention is also be made of polyethoxylated fatty amides preferably having from 2 to 30 ethylene oxide units, polyglycerolated fatty amides including on average from 1 to 5, and in particular from 1.5 to 4, glycerol groups; polyoxyethylenated fatty acid esters of sorbitan having preferably from 2 to 40 units of ethylene oxide, fatty acid esters of sucrose, polyoxyalkylenated and preferably polyoxyethylenated fatty acid esters containing from 2 to 150 mol of ethylene oxide, such as oxyethylenated plant oils.

Useful nonionic surfactants include those of the alkyl (poly)glycoside type, represented especially by the following general formula: $R_1O$—$(R_2O)_t$-$(G)_v$ in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents an alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly)glycoside surfactant may be an alkyl(poly)glucoside surfactant $C_8/C_{16}$ alkyl (poly)glucosides 1,4, and in particular decyl glucosides and caprylyl/capryl glucosides.

Useful nonionic surfactants may be chosen from polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof.

The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 2 EO (Ceteth-2) (HLB 5.3) cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3) lauryl alcohol polyoxyethylenated with 2 EO (Laureth-2) (HLB 6.1) lauryl alcohol polyoxyethylenated with 3 EO (Laureth-3) (HLB 8) lauryl alcohol polyoxyethylenated with 4 EO (Laureth-4) (HLB 9.4) lauryl alcohol polyoxyethylenated with 7 EO (Laureth-7) (HLB 12.3) lauryl alcohol polyoxyethylenated with 9 EO (Laureth-9) (HLB 13.6) lauryl alcohol polyoxyethylenated with 10 EO (Laureth-10) (HLB 13.9) lauryl alcohol polyoxyethylenated with 12 EO (Laureth-12) (HLB 14.6) lauryl alcohol polyoxyethylenated with 21 EO (Laureth-21) (HLB 15.5) lauryl alcohol polyoxyethylenated with 23 EO (Laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5)

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15). In a preferred embodiment, the hair treatment compositions include one or more nonionic surfactants chosen from polyoxyethylenated C8-C30 fatty acid esters (preferably C12-C18) of sorbitan, preferably polyoxyethylenated esters of C12-C18 fatty acids.

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids mention is made of glyceryl stearate (glyceryl mono-, di- and/or tristearate) (CTFA name: glyceryl stearate) or glyceryl ricinoleate and mixtures thereof.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Alkyl polyglucosides are a class of useful nonionic surfactants. Non-limiting examples of alkyl polyglucosides include alkyl polyglucosides having the following formula:

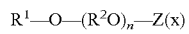

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides include lauryl glucoside, octyl glucoside, decyl glucoside, coca glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coca glucoside, and more typically lauryl glucoside. In some instances, decyl glucoside is particularly preferred.

The total amount of nonionic, if present, may vary. When present, the total amount of nonionic surfactants present may be about 0.01 to about 10 wt. %, based on the total weight of the hair treatment composition. The total amount of nonionic surfactants present may be about 0.01 to about 8 wt. %, about 0.01 to about 5 wt. %, about 0.01 to about 3 wt. %, about 0.05 to about 10 wt. %, about 0.05 to about 8 wt. %, about 0.05 to about 5 wt. %, about 0.05 to about 3 wt. %, about 0.1 to about 10 wt. %, about 0.1 to about 8 wt. %, about 0.1 to about 5 wt. %, or about 0.1 to about 3 wt. %, including any combination, sub-combination, range, or sub-range thereof by weight, based on the total weight of the hair treatment composition.

(j) Miscellaneous Ingredients

The hair treatment compositions of the instant disclosure may optionally include one or more miscellaneous ingredients. Miscellaneous ingredients are ingredients that are compatible with the hair treatment compositions and do not disrupt or materially affect the basic and novel properties of the hair treatment compositions. Miscellaneous ingredients commonly used in cosmetics and hair care products are known in the art. Non-limiting examples include preservatives, fragrances, pH adjusters, salts, antioxidants, vitamins, botanical extracts, UV filtering agents, proteins, protein hydrolysates, hydrotropes, pearlescent agents, buffers, etc.

Miscellaneous ingredients can be included, for example, in an amount of about 0.01 to about 10 wt. %, based on the total weight of the hair treatment composition. The total amount of the one or more miscellaneous ingredients may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. %, based on the total weight of the hair treatment composition.

Ratio of (c) to (d)

The ratio of the one or more cationic polymers (b) to the one or more nonionic polymers (d) is about 2.9:1 to about 1:2.9. However, the ratio may be about 2.5:1 to about 1:2.5, about 2.2:1 to about 1:2.2, about 2:1 to about 1:2, about 1.8:1 to about 1:1.8, about 1.5:1 to about 1:1.5, about 1.3:1 to about 1:1.3, about 1.2 to 1 to about 1 to 1.2 including any combination, sub-combination, range, or sub-range thereof by weight, based on the total weight of the hair treatment composition. Furthermore, in various embodiments, the ratio may be about 2.5:1 to about 1:2.9, about 2.9:1 to about 2.5:1; about 2.2:1 to 1:2.5, about 2.5:1 to about 1:2.2, about 2:1 to 1:2.2, about 2.2:1 to about 2:1, about 1.8:1 to about 1:2, about 1:2 to about 1:1.8; about 1.5:1 to about 1:2, about 1:2 to about 1:1.5, about 1.5:1 to about 1:1.5, about 1.2:1 to about 1.5:1, or about 1.5:1 to about 1:1.2, including any combination, sub-combination, range, or sub-range thereof by weight, based on the total weight of the hair treatment composition.

pH of the Hair Treatment Compositions

The pH of the hair treatment compositions is typically less than 7, i.e., the pH of the hair treatment compositions is typically somewhat acidic. For example, the pH may be about 3 to less than 7, about 3.5 to less than 7, about 4 to less than 7, about 4.5 to less than 7, about 5 to less than 7, about 3 to about 6.5, about 3.5 to about 6.5, about 4 to about 6.5, about 3 to about 6, about 3.5 to about 6, about 3.3 to about 6, about 3 to less than 6, about 3.5 to less than 6, about 3.3 to about 5, about 3.3 to about 4.5, about 3.3. to about 4.3, including any combination, sub-combination, range, or sub-range thereof.

Viscosity of the Hair Treatment Compositions

The viscosity of the hair treatment compositions is typically about 5 mPa·s to about 50,000 mPa·s at a temperature of 25° C. The viscosity may be about 10 mPa·s to about 50,000 m Pas, about 15 to about 50,000 mPa·s, about 20 to about 50,000 mPa·s, about 100 mPa·s to about 50,000 mPa·s, about 1,000 to about 50,000, about 5 mPa·s to about 25,000, about 10 to about 25,000 mPa·s, about 20 to about 25,000 mPa·s, about 100 to about 25,000 mPa·s, about 1,000 to about 25,000 mPa·s, about 5 to about 10,000 m Pas, about 15 to about 10,000 mPa·s, about 20 m Pas to 10,000 mPa·s, about 5 mPa·s to 50,000 mPa·s, about 10 mPa·s to 50,000 mPa·s, about 15 mPa·s to 50,000 mPa·s, about 20 mPa·s to 50,000 mPa·s, about 5 to 25,000 mPa·s, about 10 mPa·s to 25,000 mPa·s, about 15 to 25,000 mPa·s, about 20 mPa·s to 25,000 mPa·s, about 5 mPa·s to 10,000 mPa·s, about 10 mPa·s to 10,000 mPa·s, about 15 mPa·s to 10,000 m Pas, or about 20 to 10,000 m Pas, about 5 m Pas to about 5,000 m Pas, about 10 mPa·s to about 5,000 mPa·s, about 15 mPa·s to about 5,000 mPa·s, about 20 mPa·s to about 5,000 mps, about 5 mPa·s to about 1,000 mPa·s, about 10 mPa·s to about 1,000 m Pas, about 15 m Pas to about 1,000 m Pas, about 20 to about 1,000 mPa·s, about 5 to about 500 mPa·s, about 10 to about 500 mPa·s, about 15 to about 500 m Pas, about 20 to about 500 m Pas, or about 5 to about 250 mPa·s at a temperature of 25° C., including any combination, sub-combination, range, or sub-range thereof.

The viscosity measurements can be carried out, for example, using a Brooksfield viscometer/rheometer using a RV-3 Disk or an RV-5 Disk spindle at a particular speed, for example, 5, 10, 15, and/or 20 rpm or using a Rheomat with an M4 spindle.

Stability

The hair treatment compositions are stable and homogenous. In other words, the hair treatment compositions do not visually phase separate or develop sedimentation, and do not form visibly observable particulates. As shown the Example below, the hair treatment composition remained stable throughout the entire testing period. For instance, the hair treatment composition remained stable for at least 1 week at room temperature; the hair treatment composition remained stable for at least 8 weeks at 4° C.; the hair treatment composition remained stable for at least 8 weeks at 45° C. Accordingly, the instant disclosure relates to hair treatment compositions that remain visually homogenous and free from visual phase separation and particulate formation for at least 1 week at room temperature. Furthermore, the instant disclosure relates to hair treatment compositions that remain visually homogenous and free from visual phase separation and particulate formation for at least 8 weeks at 4° C. The instant disclosure also relates to hair treatment compositions that remain visually homogenous and free from visual phase separation and particulate formation for at least 8 weeks at 45° C.

Methods

The instant disclosure relates to methods for treating hair. The methods include applying a hair treatment composition according to the instant disclosure to the hair and subsequently rinsing the hair treatment composition from the hair.

The hair treatment compositions may be used, for example, as a conditioner composition or a conditioning mask that is applied to the hair before or after shampooing the hair; or it can be used as a conditioner composition that used without shampooing the hair. Typically, the hair treatment composition is applied to wet or damp hair, massaged into/throughout the hair, and subsequently rinsed from the hair before optionally drying and/or styling the hair. The hair treatment composition may be allowed to remain on the hair prior to rinsing for a period of time, for example, a period of time of about 10 seconds to about 10 minutes, prior to rinsing from the hair. The hair treatment composition may be allowed to remain on the hair for about 10 seconds to about 5 minutes, about 10 seconds to about 2 minutes, about 30 seconds to about 10 minutes, about 30 seconds to about 5 minutes, about 30 seconds to about 2 minutes, about 1 minute to about 10 minutes, about 1 minute to about 5 minutes, or about 1 minute to 2 abouts 2 minutes, including any combination, sub-combination, range, or sub-range thereof.

The methods of treating hair, according to the procedures discussed above, are useful for conditioning the hair. The procedures are also useful in methods for improving natural look and feel of the hair, reducing hair frizz, improving hair smoothness, hair alignment, and/or hair shine. The methods also relate to increasing the hydrophobicity of the hair. Thus, the instant disclosure relates to methods for: (a) conditioning the hair; (b) improving the look and feel of hair; (c) reducing hair frizz or propensity for frizzing; (d) improving hair smoothness, (e) improving hair alignment; (e) improving or increasing hair shine; the method comprising applying a hair treatment composition according to the instant disclosure to the hair.

Kits

The hair treatment compositions disclosed herein may be provided in a kit. For example, one or more of the hair treatment compositions of the instant disclosure may be included in a kit that also includes one or more additional hair treatment compositions, for example, one or more cleansing compositions, in particular, one or more shampoo compositions. All of the various compositions in the kit are separately contained. In some instances, the kits include one or more hair treatment compositions according to the instant disclosure and one or more shampoo compositions, wherein each of the one or more hair treatment compositions and the one or more shampoo compositions are separately contained.

EMBODIMENTS

Preferred embodiments of the disclosure are discussed throughout the instant disclosure and below.

In some instances, the hair treatment compositions of the instant disclosure comprise or consists of:
(a) about 1 to about 20 wt. %, preferably about 2 to 15 wt. %, more preferably, about 5 to about 12 wt. % of one or more fatty alcohols;
(b) about 1 to about 10 wt. %, preferably about 2 to about 8 wt. %, more preferably about 2 to about 6 wt. % of one or more cationic surfactants;
(c) about 0.1 to about 5 wt. %, preferably about 0.1 to about 3 wt. %, more preferably about 0.1 to about 2 wt. % of one or more cationic polymers;
(d) about 0.1 to about 5 wt. %, preferably about 0.1 to about 3 wt. %, more preferably about 0.1 to about 2 wt. % of one or more nonionic polymers;

wherein the weight ratio of (c) to (d) is from 2.9:1 to 1:2.9, preferably from 2.5:1 to 1:2.5, more preferably from 2:1 to 1:2; and optionally, wherein the total combined amount of (c) and (d) is less than 4 wt. %, preferably less than 3 wt. %, more preferably less than 2 wt. %;

(e) about 0.1 to less than 5 wt. %, preferably about 0.5 to about 4 wt. %, more preferably about 0.5 to about 3.5 wt. % of citric acid, a salt thereof, or a combination thereof;

(f) about 55 to about 90 wt. % of water;

(g) optionally, one or more fatty compounds other than the fatty alcohols;

(h) optionally, one or more water-soluble solvents;

(i) optionally, one or more nonionic surfactants;

(j) optionally, one or more miscellaneous ingredients;

wherein the pH of the composition is from about 3 to about 6, preferably about 3 to less than 6, more preferably about 3 to about 5, and all weight percentages are based on the total weight of the composition.

In some instances, the hair treatment compositions of the instant disclosure comprise or consists of:

(a) about 1 to about 20 wt. %, preferably about 2 to 15 wt. %, more preferably, about 5 to about 12 wt. % of one or more fatty alcohols, in particular fatty alcohols having from about 8 to about 22 carbon atoms, in particular one or more fatty alcohols chosen from decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, and a mixture thereof, preferably chosen from myristyl alcohol, lauryl alcohol, cetyl alcohol, stearyl alcohol, cetearyl alcohol, isostearyl alcohol, oleyl alcohol, isotridecyl alcohol, and a mixture thereof;

(b) about 1 to about 10 wt. %, preferably about 2 to about 8 wt. %, more preferably about 2 to about 6 wt. % of one or more cationic surfactants, in particular one or more cationic surfactants chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chlofride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof, preferably cetrimonium chloride, stearimonium chloride, behentrimonium chloride, behentrimonium methosulfate, and mixtures thereof;

(c) about 0.1 to about 5 wt. %, preferably about 0.1 to about 3 wt. %, more preferably about 0.1 to about 2 wt. % of one or more cationic polymers, in particular, cationic cellulose derivatives (polyquaternium-10), quaternized hydroxyethyl cellulose, cationic starch derivatives, cationic guar gum derivatives, cationic proteins and cationic protein hydrolysates, quaternary diammonium polymers, copolymers of acrylamide and dimethyldiallyammonium chloride, polyquaterniums (polyquatemium-10), and a mixture thereof, more preferably, cationic cellulose derivative and/or polyquaterniums, such as polyquaternium-10;

(d) about 0.1 to about 5 wt. %, preferably about 0.1 to about 3 wt. %, more preferably about 0.1 to about 2 wt. % of one or more nonionic polymers, in particular, polysaccharides, polysaccharide derivatives (e.g., guar gum, guar derivatives, cellulose gum, cellulose derivatives, starch, starch derivatives), homopolymers and copolymers of ethylene oxide having a molar mass equal to or greater than 10,000 g/mol, polyvinyl alcohols, homopolymers and copolymers of vinylpyrrolidone, homopolymers and copolymers of vinylcaprolactam, homopolymers and copolymers of polyvinyl methyl ether, and mixtures thereof, preferably polysaccharides and polysaccharide derivatives, more preferably guar gum and/or guar derivatives, especially hydroxypropyl guar;

wherein the weight ratio of (c) to (d) is from 2.9:1 to 1:2.9, preferably from 2.5:1 to 1:2.5, more preferably from 2:1 to 1:2; and optionally, wherein the total combined amount of (c) and (d) is less than 4 wt. %, preferably less than 3 wt. %, more preferably less than 2 wt. %;

(e) about 0.1 to less than 5 wt. %, preferably about 0.5 to about 4 wt. %, more preferably about 0.5 to about 3.5 wt. % of citric acid, a salt thereof, or a combination thereof;

(f) about 55 to about 90 wt. %, preferably about 60 to about 85 wt. %, more preferably about 65 to about 80 wt. % of water;

(g) optionally, one or more fatty compounds other than the fatty alcohols of (a), for example, from about 0.01 to about 10 wt. %, more preferably about 0.1 to about 8 wt. %, more preferably about 0.1 to about 6 wt. %, in particular selected from oils, waxes, alkanes (paraffins), fatty acids, fatty esters, triglyceride compounds, lanolin, hydrocarbons, derivatives thereof, and mixtures thereof;

(h) optionally, one or more water-soluble solvents, for example, from about 0.01 to 10 wt. %, preferably 0.1 to about 8 wt. %, more preferably about 0.1 to about 6 wt. % of one or more water-soluble solvents chosen from glycerin, alcohols (for example, C1-15, C1-10, or C1-4 alcohols), organic solvents, polyols (polyhydric alcohols), glycols (e.g., butylene glycol, caprylyl glycol, etc.), and a mixture thereof, preferably glycerin and/or one or more C1-4 alcohols;

(i) optionally, one or more nonionic surfactants, for example, about 0.01 to about 10 wt. %, preferably about 0.1 to about 8 wt. %, more preferably about 0.1 to about 6 wt. % of one or more nonionic surfactants, preferably wherein one or more of the one or more nonionic surfactants is a polyoxyethylenated C8-C30 fatty acid esters (preferably C12-C18) of sorbitan;

(j) optionally, about 0.01 to about 10 wt. %, preferably about 0.1 to about 8 wt. %, more preferably about 0.1 to about 5 wt. % of one or more miscellaneous ingredients;

wherein the composition has a pH of about 3 to about 6, preferably about 3 to less than 6, more preferably about 3 to about 5, and all weight percentages are based on the total weight of the composition.

In the embodiment above, the one or more fatty alcohols in the hair treatment composition may be the predominant ingredient, other than water. In other words, the hair treatment composition may include a higher total amount of the one or more fatty alcohols than any other ingredient, or class of ingredients (other than water). Accordingly, the hair treatment composition may include a higher total amount of the one or more fatty alcohols (a) than the total amount of the one or more cationic surfactants (b); a higher total amount of the one or more fatty alcohols (a) than the total amount of the one or more cationic polymers (c); a higher total amount of the one or more fatty alcohols (a) than the total amount of the one or more nonionic polymer (d); a higher total amount of the one or more fatty alcohols (a) than the total amount of citric acid, salt thereof, and/or combination thereof (e); a higher total amount of the one or more fatty alcohols (a) than the total amount of the one or more fatty compounds other than fatty alcohols (g); a higher total amount of the one or more fatty alcohols (a) than the total amount of the one or more water-soluble solvents (h); a higher total amount of the one or more fatty alcohols (a) than the total amount of the one or more nonionic surfactants (i).

In some instances, the hair treatment compositions may have a higher total amount of the one or more fatty alcohols (a) than the total combined weight percent of the one or more cationic surfactants (b) and the one or more nonionic surfactants (i). Furthermore, in some instances, the hair treatment composition may have a higher total amount of the one or more fatty alcohols (a) than the total combined weight percent of the one or more cationic surfactants (b), the one or more nonionic surfactants (i), and any additional surfactants that may optionally be present, e.g., amphoteric/zwitterionic surfactants.

In some instances, the weight ratio of the total amount of the one or more fatty alcohols (a) to the one or more cationic surfactants (b) is at least 1.5:1 ((a):(b)). Furthermore, the weight ratio of the total amount of the one or more fatty alcohols (a) to the one or more cationic surfactants (b) may be at least 1.8:1, 1.9:1, 2:1, 2.1:1, or 2.2:1 ((a):(b)). Thus, the ratio of (a):(b) may be from 1.8:1 to about 5:1, about 1.9:1 to about 5:1, about 2:1 to about 5:1, about 2.1:1 to about 5:1, about 2.2:1 to about 5:1, about 2.2:1 to about 5:1, about 1.8:1 to about 4:1, about 1.9:1 to about 4:1, about 2:1 to about 4:1, about 2.1:1 to about 4:1, about 2.2:1 to about 4:1, about 2.2:1 to about 4:1, about 1.8:1 to about 3:1, about 1.9:1 to about 3:1, about 2:1 to about 3:1, about 2.1:1 to about 3:1, about 2.2:1 to about 3:1, about 2.2:1 to about 3:1, including any combination, sub-combination, range, or sub-range thereof by weight, based on the total weight of the hair treatment composition.

In some instances, the hair treatment compositions of the instant disclosure comprise or consists of:

(a) about 1 to about 20 wt. %, preferably about 2 to 15 wt. %, more preferably, about 5 to about 12 wt. % of one or more fatty alcohols chosen from myristyl alcohol, lauryl alcohol, cetyl alcohol, stearyl alcohol, cetearyl alcohol, isostearyl alcohol, oleyl alcohol, isotridecyl alcohol, and a mixture thereof, preferably chosen from stearyl alcohol, cetearyl alcohol, cetyl alcohol, and mixtures thereof;

(b) about 1 to about 10 wt. %, preferably about 2 to about 8 wt. %, more preferably about 2 to about 6 wt. % of one or more cationic surfactants chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chlofride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof, preferably cetrimonium chloride, stearimonium chloride, behentrimonium chloride, behentrimonium methosulfate, and mixtures thereof;

(c) about 0.1 to about 5 wt. %, preferably about 0.1 to about 3 wt. %, more preferably about 0.1 to about 2 wt. % of one or more cationic polymers chosen from cationic polysaccharides, preferably cationic cellulose derivatives (e.g., polyquatemium-10);

(d) about 0.1 to about 5 wt. %, preferably about 0.1 to about 3 wt. %, more preferably about 0.1 to about 2 wt. % of one or more nonionic polymers chosen from polysaccharides and polysaccharide derivatives, preferably, guar gum, guar derivatives, cellulose gum, cellulose derivatives, starch, starch derivatives, more preferably, hydroxypropyl guar;
wherein the weight ratio of (c) to (d) is from 2.9:1 to 1:2.9, preferably from 2.5:1 to 1:2.5, more preferably from 2:1 to 1:2; and
optionally, wherein the total combined amount of (c) and (d) is less than 4 wt. %, preferably less than 3 wt. %, more preferably less than 2 wt. %;

(e) about 0.1 to less than 5 wt. %, preferably about 0.5 to about 4 wt. %, more preferably about 0.5 to about 3.5 wt. % of citric acid, a salt thereof, or a combination thereof;

(f) about 55 to about 90 wt. %, preferably about 60 to about 85 wt. %, more preferably about 65 to about 80 wt. % of water;

(g) optionally, one or more fatty compounds other than the fatty alcohols of (a), for example, from about 0.01 to about 10 wt. %, more preferably 0.1 to about 8 wt. %, more preferably about 0.1 to about 6 wt. %, in particular selected from oils, waxes, alkanes (paraffins), fatty acids, fatty esters, triglyceride compounds, lanolin, hydrocarbons, derivatives thereof, and mixtures thereof;

(h) optionally, one or more water-soluble solvents, for example, from about 0.01 to 10 wt. %, preferably 0.1 to about 8 wt. %, more preferably about 0.1 to about 6 wt. % of one or more water-soluble solvents chosen from glycerin, alcohols (for example, C1-15, C1-10, or C1-4 alcohols), organic solvents, polyols (polyhydric alcohols), glycols (e.g., butylene glycol, caprylyl glycol, etc.), and a mixture thereof, preferably glycerin and/or one or more C1-4 alcohols;

(i) optionally, one or more nonionic surfactants, for example, about 0.01 to about 10 wt. %, preferably about 0.1 to about 8 wt. %, more preferably about 0.1 to about 6 wt. % of one or more nonionic surfactants, preferably wherein one or more of the one or more nonionic surfactants is a polyoxyethylenated C8-C30 fatty acid esters (preferably C12-C18) of sorbitan;

(j) optionally, about 0.01 to about 10 wt. %, preferably about 0.1 to about 8 wt. %, more preferably about 0.1 to about 5 wt. % of one or more miscellaneous ingredients;

wherein the composition has a pH of about 3 to about 6, preferably about 3 to less than 6, more preferably about 3 to about 5, and all weight percentages are based on the total weight of the composition.

In the embodiment above, the one or more fatty alcohols in the hair treatment composition may be the predominant ingredient, other than water. In other words, the hair treatment composition may include a higher total amount of the one or more fatty alcohols than any other ingredient, or class of ingredients (other than water). Accordingly, the hair treatment composition may include a higher total amount of the one or more fatty alcohols (a) than the total amount of the one or more cationic surfactants (b); a higher total amount of the one or more fatty alcohols (a) than the total amount of the one or more cationic polymers (c); a higher total amount of the one or more fatty alcohols (a) than the total amount of the one or more nonionic polymer (d); a higher total amount of the one or more fatty alcohols (a) than the total amount of citric acid, salt thereof, and/or combination thereof (e); a higher total amount of the one or more fatty alcohols (a) than the total amount of the one or more fatty compounds other than fatty alcohols (g); a higher total amount of the one or more fatty alcohols (a) than the total amount of the one or more water-soluble solvents (h); a higher total amount of the one or more fatty alcohols (a) than the total amount of the one or more nonionic surfactants (i).

In the embodiment above, the hair treatment compositions may have a higher total amount of the one or more fatty alcohols (a) than the total combined weight percent of the one or more cationic surfactants (b) and the one or more nonionic surfactants (i). Furthermore, in some instances, the hair treatment composition may have a higher total amount of the one or more fatty alcohols (a) than the total combined weight percent of the one or more cationic surfactants (b), the one or more nonionic surfactants (i), and any additional surfactants that may optionally be present, e.g., amphoteric/zwitterionic surfactants.

In the embodiment above, the weight ratio of the total amount of the one or more fatty alcohols (a) to the one or more cationic surfactants (b) is at least 1.5:1 ((a):(b)). Furthermore, the weight ratio of the total amount of the one or more fatty alcohols (a) to the one or more cationic surfactants (b) may be at least 1.8:1, 1.9:1, 2:1, 2.1:1, or 2.2:1 ((a):(b)). Thus, the ratio of (a):(b) may be from 1.8:1 to about 5:1, about 1.9:1 to about 5:1, about 2:1 to about 5:1, about 2.1:1 to about 5:1, about 2.2:1 to about 5:1, about 2.2:1 to about 5:1, about 1.8:1 to about 4:1, about 1.9:1 to about 4:1, about 2:1 to about 4:1, about 2.1:1 to about 4:1, about 2.2:1 to about 4:1, about 2.2:1 to about 4:1, about 1.8:1 to about 3:1, about 1.9:1 to about 3:1, about 2:1 to about 3:1, about 2.1:1 to about 3:1, about 2.2:1 to about 3:1, about 2.2:1 to about 3:1, including any combination, sub-combination, range, or sub-range thereof by weight, based on the total weight of the hair treatment composition.

In some instances, the hair treatment compositions of the instant disclosure consists of:

(a) about 1 to about 20 wt. %, preferably about 2 to 15 wt. %, more preferably, about 5 to about 12 wt. % of one or more fatty alcohols chosen from myristyl alcohol, lauryl alcohol, cetyl alcohol, stearyl alcohol, cetearyl alcohol, isostearyl alcohol, oleyl alcohol, isotridecyl alcohol, and a mixture thereof, preferably chosen from stearyl alcohol, cetearyl alcohol, cetyl alcohol, and mixtures thereof;

(b) about 1 to about 10 wt. %, preferably about 2 to about 8 wt. %, more preferably about 2 to about 6 wt. % of one or more cationic surfactants chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chlofride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof, preferably cetrimonium chloride, stearimonium chloride, behentrimonium chloride, behentrimonium methosulfate, and mixtures thereof;

(c) about 0.1 to about 5 wt. %, preferably about 0.1 to about 3 wt. %, more preferably about 0.1 to about 2 wt. % of one or more cationic polymers chosen from cationic polysaccharides, preferably cationic cellulose derivatives (e.g., polyquatemium-10);

(d) about 0.1 to about 5 wt. %, preferably about 0.1 to about 3 wt. %, more preferably about 0.1 to about 2 wt. % of one or more nonionic polymers chosen from polysaccharides and polysaccharide derivatives, preferably, guar gum, guar derivatives, cellulose gum, cellulose derivatives, starch, starch derivatives, more preferably, hydroxypropyl guar;

wherein the weight ratio of (c) to (d) is from 2.9:1 to 1:2.9, preferably from 2.5:1 to 1:2.5, more preferably from 2:1 to 1:2; and optionally, wherein the total combined amount of (c) and (d) is less than 4 wt. %, preferably less than 3 wt. %, more preferably less than 2 wt. %;

(e) about 0.1 to less than 5 wt. %, preferably about 0.5 to about 4 wt. %, more preferably about 0.5 to about 3.5 wt. % of citric acid, a salt thereof, or a combination thereof;

(f) about 55 to about 90 wt. %, preferably about 60 to about 85 wt. %, more preferably about 65 to about 80 wt. % of water;

(g) optionally, one or more fatty compounds other than the fatty alcohols of (a), for example, from about 0.01 to about 10 wt. %, more preferably about 0.1 to about 8 wt. %, more preferably about 0.1 to about 6 wt. %, in particular selected from oils, waxes, alkanes (paraffins), fatty acids, fatty esters, triglyceride compounds, lanolin, hydrocarbons, derivatives thereof, and mixtures thereof;

(h) optionally, one or more water-soluble solvents, for example, from about 0.01 to 10 wt. %, preferably 0.1 to about 8 wt. %, more preferably about 0.1 to about 6 wt. % of one or more water-soluble solvents chosen from glycerin, alcohols (for example, C1-15, C1-10, or C1-4 alcohols), organic solvents, polyols (polyhydric alcohols), glycols (e.g., butylene glycol, caprylyl glycol, etc.), and a mixture thereof, preferably glycerin and/or one or more C1-4 alcohols;
(i) optionally, one or more nonionic surfactants, for example, about 0.01 to about 10 wt. %, preferably about 0.1 to about 8 wt. %, more preferably about 0.1 to about 6 wt. % of one or more nonionic surfactants, preferably wherein one or more of the one or more nonionic surfactants is a polyoxyethylenated C8-C30 fatty acid esters (preferably C12-C18) of sorbitan;
(j) optionally, about 0.01 to about 10 wt. %, preferably about 0.1 to about 8 wt. %, more preferably about 0.1 to about 5 wt. % of one or more miscellaneous ingredients;
wherein the composition has a pH of about 3 to about 6, preferably about 3 to less than 6, more preferably about 3 to about 5, and all weight percentages are based on the total weight of the composition.

In the embodiment above, the one or more fatty alcohols in the hair treatment composition may be the predominant ingredient, other than water. In other words, the hair treatment composition may include a higher total amount of the one or more fatty alcohols than any other ingredient, or class of ingredients (other than water). Accordingly, the hair treatment composition may include a higher total amount of the one or more fatty alcohols (a) than the total amount of the one or more cationic surfactants (b); a higher total amount of the one or more fatty alcohols (a) than the total amount of the one or more cationic polymers (c); a higher total amount of the one or more fatty alcohols (a) than the total amount of the one or more nonionic polymer (d); a higher total amount of the one or more fatty alcohols (a) than the total amount of citric acid, salt thereof, and/or combination thereof (e); a higher total amount of the one or more fatty alcohols (a) than the total amount of the one or more fatty compounds other than fatty alcohols (g); a higher total amount of the one or more fatty alcohols (a) than the total amount of the one or more water-soluble solvents (h); a higher total amount of the one or more fatty alcohols (a) than the total amount of the one or more nonionic surfactants (i).

In the embodiment above, the hair treatment compositions may have a higher total amount of the one or more fatty alcohols (a) than the total combined weight percent of the one or more cationic surfactants (b) and the one or more nonionic surfactants (i). Furthermore, in some instances, the hair treatment composition may have a higher total amount of the one or more fatty alcohols (a) than the total combined weight percent of the one or more cationic surfactants (b), the one or more nonionic surfactants (i), and any additional surfactants that may optionally be present, e.g., amphoteric/zwitterionic surfactants.

In the embodiment above, the weight ratio of the total amount of the one or more fatty alcohols (a) to the one or more cationic surfactants (b) is at least 1.5:1 ((a):(b)). Furthermore, the weight ratio of the total amount of the one or more fatty alcohols (a) to the one or more cationic surfactants (b) may be at least 1.8:1, 1.9:1, 2:1, 2.1:1, or 2.2:1 ((a):(b)). Thus, the ratio of (a):(b) may be from 1.8:1 to about 5:1, about 1.9:1 to about 5:1, about 2:1 to about 5:1, about 2.1:1 to about 5:1, about 2.2:1 to about 5:1, about 2.2:1 to about 5:1, about 1.8:1 to about 4:1, about 1.9:1 to about 4:1, about 2:1 to about 4:1, about 2.1:1 to about 4:1, about 2.2:1 to about 4:1, about 2.2:1 to about 4:1, about 1.8:1 to about 3:1, about 1.9:1 to about 3:1, about 2:1 to about 3:1, about 2.1:1 to about 3:1, about 2.2:1 to about 3:1, about 2.2:1 to about 3:1, including any combination, sub-combination, range, or sub-range thereof by weight, based on the total weight of the hair treatment composition.

EXAMPLES

Example 1

Inventive Compositions

| | | | A | B | C |
|---|---|---|---|---|---|
| (a) | Fatty Alcohol | STEARYL ALCOHOL AND CETEARYL ALCOHOL | 8.8 | 8.8 | 8.8 |
| (b) | Cationic Surfactant | BEHENTRIMONIUM CHLORIDE | 3.6 | 3.6 | 3.6 |
| (c) | Cationic Polymer | POLYQUATERNIUM-10 | 0.3 | 0.3 | 0.3 |
| (d) | Nonionic Polymer | HYDROXYPROPYL GUAR | 0.2 | 0.4 | 0.2 |
| (e) | Citric Acid | CITRIC ACID | 1.6 | 1.6 | 1.6 |
| | Sodium Citrate | SODIUM CITRATE | 1.4 | 1.4 | 1.4 |
| (g) | Fatty Compounds | CETYL ESTERS | 1.5 | 1.5 | 1.5 |
| (h) | Water-Soluble Solvent | GLYCERIN AND ISOPROPYL ALCOHOL | 5.8 | 5.8 | 5.8 |
| (i) | Nonionic Surfactant | POLYSORBATE 20 | 2.5 | 2.5 | 5.0 |
| (j) | Miscellaneous | e.g., preservatives, fragrances, pH adjusters, extracts, chelating agents, antioxidants, etc. | ≤4 | ≤4 | ≤4 |
| (f) | Water | WATER | QS100 | QS100 | QS100 |
| | pH | | 3.7 | 3.7 | 3.7 |

Example 2

Comparative Compositions

| | | Inventive | Comparative | | | | | | | | | | | | | |
|---|---|---|---|---|---|---|---|---|---|---|---|---|---|---|---|---|
| | | A | C1 | C2 | C3 | C4 | C5 | C6 | C7 | C8 | C9 | C10 | C11 | C12 | C13 | C14 |
| (a) | Cetearyl Alcohol & Stearyl Alcohol | 8.8 | — | 8.8 | 8.8 | 8.8 | 8.8 | 8.8 | 8.8 | 8.8 | 8.8 | 8.8 | 8.8 | 8.8 | 8.8 | 8.8 |
| (b) | Behentrimonium Chloride | 3.6 | 3.6 | — | 3.6 | 3.6 | 3.6 | 3.6 | 3.6 | 3.6 | 3.6 | 3.6 | 3.6 | 3.6 | 3.6 | 3.6 |
| (c) | PQ-10 | 0.3 | 0.3 | 0.3 | — | 0.3 | 0.3 | 0.3 | 1 | 0.1 | 1 | 3 | 0.3 | 0.3 | 0.3 | 0.3 |
| (d) | Hydroxypropyl Guar | 0.2 | 0.2 | 0.2 | 0.2 | — | 0.2 | 0.2 | 0.1 | 1 | 3 | 1 | 0.2 | 0.2 | 0.2 | 0.2 |

-continued

| | | Inventive | Comparative | | | | | | | | | | | | | |
|---|---|---|---|---|---|---|---|---|---|---|---|---|---|---|---|---|
| | | A | C1 | C2 | C3 | C4 | C5 | C6 | C7 | C8 | C9 | C10 | C11 | C12 | C13 | C14 |
| (e) | Citric Acid | 1.6 | 1.6 | 1.6 | 1.6 | 1.6 | — | 1.6 | 1.6 | 1.6 | 1.6 | 1.6 | 1.6 | 0.1 | 3 | 1 |
| | Sodium Citrate | 1.4 | 1.4 | 1.4 | 1.4 | 1.4 | 1.4 | — | 1.4 | 1.4 | 1.4 | 1.4 | 0.1 | 1.4 | 1 | 3 |
| (g) | Cetyl Esters | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| (h) | Glycerin and Isopropy Alcohol | 5.8 | 5.8 | 5.8 | 5.8 | 5.8 | 5.8 | 5.8 | 5.8 | 5.8 | 5.8 | 5.8 | 5.8 | 5.8 | 5.8 | 5.8 |
| (i) | Polysorbate 20 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 |
| (j) | Miscellaneous | ≤4 | ≤4 | ≤4 | ≤4 | ≤4 | ≤4 | ≤4 | ≤4 | ≤4 | ≤4 | ≤4 | ≤4 | ≤4 | ≤4 | ≤4 |
| (f) | Water | QS | QS | QS | QS | QS | QS | QS | QS | QS | QS | QS | QS | QS | QS | QS |
| | (c):(d) | 3:2 | 3:2 | 3:2 | 0:2 | 3:0 | 3:2 | 3:2 | 10:1 | 1:10 | 1:3 | 3:1 | 3:2 | 3:2 | 3:2 | 3:2 |
| | (e):(f) | 8:7 | 8:7 | 8:7 | 8:7 | 8:7 | 0:7 | 8:0 | 8:7 | 8:7 | 8:7 | 8:7 | 16:1 | 1:14 | 3:1 | 1:3 |
| | pH | 3.7 | NA* | NA* | 3.7 | 3.6 | 6.7 | 2.1 | 3.6 | 3.7 | 3.7 | 3.9 | 2.4 | 6.2 | 2.8 | NA* |

*NA - Small particles immediately appeared at the time of formulation (the compositions were not stable). Therefore, an accurate pH could not be ascertained.

Example 3

Stability Data

The compositions of Example 2 were subjected to stability studies. The stability of the compositions was visually accessed upon initial manufacture of the composition ($T_0$). The compositions were again evaluated after one week of freeze-thaw testing (1 W FT). The compositions were placed in a stability chamber and subjected to temperature fluctuation at 12-hour intervals. For 12 hours, the compositions were held at −10° C. For the next 12 hours, the compositions were held at 25° C. The cycle was repeated 7 times (for 1 week). The compositions were separately evaluated after 8 weeks in storage at 4° C. (8 W 45° C.), and after 8 weeks in storage at 45° C. (8 W 4° C.). The results are presented in the table below.

| | A | C1 | C2 | C3 | C4 | C5 | C6 | C7 | C8 | C9 | C10 | C11 | C12 | C13 | C14 |
|---|---|---|---|---|---|---|---|---|---|---|---|---|---|---|---|
| STABILITY at T0 | Y | N* | N** | Y | Y | Y | Y | Y | Y | Y | Y | Y | Y | Y | N* |
| STABILITY at 1 W FT | Y | N/A | N/A | Y | N** | N** | N*** | Y | N** | N*** | N*** | N*** | N** | N** | N/A |
| STABILITY at 8 W 45° C. | Y | N/A | N/A | Y | N** | N** | N*** | Y | N** | N*** | N*** | N*** | N** | N** | N/A |
| STABILITY at 8 W 4° C. | Y | N/A | N/A | Y | Y | N** | Y | Y | Y | N*** | N*** | Y | N** | Y | N/A |

Y Yes, stable
*Small particles generated immediately upon formulation
**Formula separated after formulation
***Formula showed serious aesthetic changes such as color and odor
N/A = 8 week stability was not performed due to instability at T = 0

As shown above, Inventive Composition A was stable under all testing conditions. None of the comparative compositions were stable under all testing conditions except Comparative Composition C-7.

Example 4

Sensorial Data

The compositions of Example 2 that were at least initially stable were tested to determine their benefits to hair. Highly bleached Caucasian hair swatches (SA40, 2.7 g, 27 cm) were used in the testing. Equal amounts of each composition tested (about 1.2 grams) were applied to damp hair swatches, massaged into the hair, and allowed to remain on the hair for 5 minutes. After 5 minutes, the compositions were rinsed from the hair swatches with room temperature tap water. After removing excess water from the hair swatches, they hair swatches were washed with a standard basic shampoo. After washing, the swatches were initially towel dried and then completely dried using a blow dryer. Throughout this process expert evaluators tested the hair swatches for a variety of sensorial effects: wet smoothness, wet combing, dry smoothness, dry combing, dry strength, and dry alignment. Specifically, the evaluators assessed whether sensorial effects were better than the benchmark (Inventive Composition A), worse than the benchmark, or substantially identical to the benchmark. The results are presented in the table below.

|  | A | C1 | C2 | C3 | C4 | C5 | C6 | C7 | C8 | C9 | C10 | C11 | C12 | C13 | C14 |
|---|---|---|---|---|---|---|---|---|---|---|---|---|---|---|---|
| Wet Smoothness | B | NA | NA | - | = | + | - | + | - | + | - | = | + | -- | NA |
| Wet combing | B | NA | NA | - | - | = | - | = | - | = | - | = | + | -- | NA |
| Dry Smoothness | B | NA | NA | = | = | = | + | + | + | - | + | + | - | - | NA |
| Dry Combing | B | NA | NA | - | = | = | + | + | - | - | -- | -- | - | + | NA |
| Dry Strength | B | NA | NA | + | -- | -- | - | -- | - | + | + | - | + | = | NA |
| Dry Alignment | B | NA | NA | - | -- | -- | = | -- | = | - | = | - | = | - | NA |

\* B = Benchmark (inventive)
\*\* NA = not evaluated due to instability of the composition made
++ Better than the benchmark
+ Somewhat better than the benchmark
= Same as the benchmark
- Somewhat inferior than the benchmark
-- Inferior than the benchmark Inventive Composition A provided the most balanced performance on both wet and dry hair, i.e., it provided the best results across the spectrum of all attributes tested. All comparative compositions failed to provide a full spectrum of improvements. For example, Comparative Composition $C_7$ showed improvements in smoothness and dry combining, but resulted in significant reductions in dry strength and dry alignment. Inferiority with respect to dry alignment results in a perception of the hair being dry and weakened, which is unfavorable to consumers. The complete and balanced nature of the various attributes provided to hair by Inventive Composition A is significant and surprisingly superior to that provided by the comparative compositions.

Definitions

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular. Thus, the term "a mixture thereof" is interchangeable with "mixtures thereof." Throughout the disclosure, the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Some of the various categories of components identified may overlap. In such cases where overlap may exist and the composition/product includes two overlapping components (or more than two overlapping components), an overlapping component does not represent more than one component. For example, a component such as a fatty ester may fall within a definition of a "fatty compound" and within a definition of an "emulsifier." If a particular composition/product requires both a fatty compound component and an emulsifier component, a single fatty ester can serve as only a fatty compound or an (a single fatty ester cannot serve as both the fatty compound and the emulsifier).

All percentages, parts and ratios herein are based upon the total weight of the compositions of the present invention, unless otherwise indicated.

An "alkyl radical" is a linear or branched saturated hydrocarbon-based group, particularly $C_1$-$C_8$, more particularly $C_1$-$C_6$, preferably $C_1$-$C_4$ such as methyl, ethyl, isopropyl and tert-butyl;

An "alkoxy radical" is a alkyl-oxy wherein alkyl is as described herein before;

An "alkenyl radical" is a linear or branched unsaturated hydrocarbon-based group, particularly $C_2$-$C_8$, more particularly $C_2$-$C_6$, preferably $C_2$-$C_4$ such as ethylenyl, propylenyl;

An "alkylene radical" is a linear or branched divalent saturated $C_1$-$C_8$, in particular $C_1$-$C_6$, preferably $C_1$-$C_4$ hydrocarbon-based group such as methylene, ethylene or propylene.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention). Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment composition comprising:
   (a) about 6 to about 12 wt. % of one or more fatty alcohols having a carbon chain of 12 to 22 carbon atoms;
   (b) about 1 to about 10 wt. % of one or more cationic surfactants chosen from cetrimonium chloride, stearimonium chloride, behentrimonium chloride, behentrimonium methosulfate, or mixtures thereof;
   (c) about 0.1 to about 3 wt. % of polyquaternium-10;
   (d) about 0.1 to about 3 wt. % of hydroxypropyl guar;
      wherein (c) and (d) are in a combined amount of less than 4 wt. % and in a weight ratio of 2:1 to 1:2 ((c):(d));
   (e) about 0.2 to about 3.5 wt. % of a combination of citric acid and one or more salts of citric acid;
   (f) about 55 to about 90 wt. % of water;
   (g) about 1 to about 5 wt. % of one or more fatty esters;
   (h) one or more water-soluble solvents chosen from glycerin, C1-6 mono-alcohols, polyols, glycols, or mixtures thereof; and
   (i) one or more nonionic surfactants;
      wherein the hair treatment composition is a water-in-oil emulsion,
      remains free from visual phase separation and particulate formation for at least 8 weeks at 4° C. and at 45° C.,
      is free from silicones,
      has a pH of about 3.3 to about 4.5, and
      all weight percentages are based on the total weight of the hair treatment composition.

2. The hair treatment composition of claim 1, wherein the water is in an amount of about 70 to about 80 wt. %, based on the total weight of the hair treatment composition.

3. The hair treatment composition of claim 1, wherein the one or more fatty alcohols are chosen from cetearyl alcohol, stearyl alcohol, or a mixture thereof.

4. The hair treatment composition of claim 1, wherein the one or more water-soluble solvents are in an amount of about 2 to 10 wt. %, based on the total weight of the hair treatment composition.

5. The hair treatment composition of claim 4, wherein the one or more water-soluble solvents are chosen from glycerin, isopropyl alcohol, or a mixture thereof.

6. The hair treatment composition of claim 1, wherein the one or more nonionic surfactants are in an amount of about 0.1 to about 5 wt. %, based on the total weight of the hair treatment composition.

7. The hair treatment composition of claim 1, wherein the one or more nonionic surfactants are chosen from polyoxyethylenated fatty acid esters of sorbitan.

8. The hair treatment composition of claim 7, wherein the polyoxyethylenated fatty acid esters of sorbitan have from 2 to 40 units of ethylene oxide.

9. The hair treatment composition of claim 7, wherein the polyoxyethylenated fatty acid esters of sorbitan are chosen from polyoxyethylenated C12-C18 fatty acid esters of sorbitan.

10. The hair treatment composition of claim 9, wherein the polyoxyethylenated C12-C18 fatty acid esters of sorbitan are chosen from polysorbate-21, polysorbate-20, polysorbate-40, polysorbate-60, polysorbate-61, polysorbate-80, or mixtures thereof.

11. A hair treatment composition comprising:
   (a) about 6 to about 12 wt. % of one or more fatty alcohols having a carbon chain of 12 to 22 carbon atoms;
   (b) about 1 to about 10 wt. % of behentrimonium chloride;
   (c) about 0.2 to about 2 wt. % of polyquaternium-10;
   (d) about 0.2 to about 2 wt. % of hydroxypropyl guar;
      wherein (c) and (d) are in a combined amount of less than 4 wt. % and in a weight ratio of 2:1 to 1:2 ((c):(d));
   (e) about 1 to about 3.5 wt. % of a combination of citric acid and sodium citrate;
   (f) about 70 to about 80 wt. % of water;
   (g) about 1 to about 5 wt. % of one or more fatty compounds;

(h) about 2 to about 10 wt. % of one or more water-soluble solvents chosen from glycerin, C1-6 mono-alcohols, polyols, glycols, or mixtures thereof; and (i) about 0.1 to about 5 wt. % of one or more nonionic surfactants;

wherein the hair treatment composition is a water-in-oil emulsion, has a pH of about 3.3 to about 4.5, remains free from visual phase separation and particulate formation for at least 8 weeks at 4° C. and at 45° C., and all weight percentages are based on the total weight of the composition.

12. The hair treatment composition of claim 11, wherein the one or more fatty alcohols are chosen from cetearyl alcohol, stearyl alcohol, or a mixture thereof.

13. The hair treatment composition of claim 12, wherein the one or more fatty compounds are chosen from fatty esters.

14. A hair treatment composition consisting of:
(a) about 6 to about 12 wt. % of one or more fatty alcohols having a carbon chain of 12 to 22 carbon atoms;
(b) about 1 to about 10 wt. % of one or more cationic surfactants selected from the group consisting of cetrimonium chloride, stearimonium chloride, behentrimonium chloride, behentrimonium methosulfate, and mixtures thereof;
(c) about 0.2 to about 2 wt. % of polyquaternium-10;
(d) about 0.2 to about 2 wt. % of hydroxypropyl guar; wherein (c) and (d) are in a combined amount of less than 4 wt. % and a weight ratio of 2:1 to 1:2 ((c):(d));
(e) about 1 to about 3.5 wt. % of a combination of citric acid and sodium citrate;
(f) about 70 to about 80 wt. % of water;
(g) about 1 to about 5 wt. % of one or more fatty compounds;
(h) about 2 to about 10 wt. % of one or more water-soluble solvents selected from the group consisting of glycerin, C1-6 mono-alcohols, polyols, glycols, and mixtures thereof;
(i) about 0.1 to about 5 wt. % of one or more nonionic surfactants, wherein at least one of the one or more nonionic surfactants is a polyoxyethylenated fatty acid ester of sorbitan; and
(j) about 0.1 to about 5 wt. % of one or more miscellaneous ingredients;

wherein the hair treatment composition is in the form of a water-in-oil emulsion, has a pH of about 3.3 to about 4.5, remains free from visual phase separation and particulate formation for at least 8 weeks at 4° C. and at 45° C., and all weight percentages are based on the total weight of the composition.

15. The hair treatment composition of claim 7, wherein the one or more miscellaneous ingredients are selected from the group consisting of preservatives, fragrances, pH adjusters, salts, antioxidants, vitamins, botanical extracts, and mixtures thereof.

16. A method for conditioning hair comprising applying the hair treatment composition of claim 1 to the hair.

17. A method for conditioning hair comprising applying the hair treatment composition of claim 11 to the hair.

18. A method for conditioning hair comprising applying the hair treatment composition of claim 14 to the hair.

* * * * *